(12) United States Patent
DeLuca et al.

(10) Patent No.: US 8,785,422 B2
(45) Date of Patent: Jul. 22, 2014

(54) A-RING MODIFIED 19-NOR-VITAMIN D ANALOGS AND THEIR USES

(71) Applicant: Wisconsin Alumni Research Foundation, Madison, WI (US)

(72) Inventors: Hector F. DeLuca, Deerfield, WI (US); Margaret Clagett-Dame, Deerfield, WI (US); Lori A. Plum, Arena, WI (US); Agnieszka Glebocka, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/828,168

(22) Filed: Mar. 14, 2013

(65) Prior Publication Data
US 2013/0331459 A1 Dec. 12, 2013

Related U.S. Application Data

(60) Provisional application No. 61/656,157, filed on Jun. 6, 2012.

(51) Int. Cl.
*A61K 31/592* (2006.01)
*A61K 31/593* (2006.01)
*C07C 401/00* (2006.01)

(52) U.S. Cl.
USPC .......................................... 514/167; 552/653

(58) Field of Classification Search
USPC .......................................... 514/167; 552/653
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | DeLuca et al. | |
| 5,843,928 A | 12/1998 | DeLuca et al. | |
| 5,936,133 A | 8/1999 | DeLuca et al. | |
| 5,945,410 A | 8/1999 | DeLuca et al. | |
| 6,392,071 B1 | 5/2002 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 2013/0331459 A1* | 12/2013 | DeLuca et al. ................ | 514/729 |

FOREIGN PATENT DOCUMENTS

| | | |
|---|---|---|
| EP | 0184206 A2 | 6/1986 |
| WO | 03075932 A1 | 9/2003 |

OTHER PUBLICATIONS

Barrack et al. (abstract, Journal of Organic Chemistry (1988), 53(8), 1790-6ACCESSION No. 1988:167787 CAPLUS; Document No. 108:167787; Original Reference No. 108:27601a, 27604a, (Journal of Organic Chemistry (1988), 53(8)).*

(Continued)

*Primary Examiner* — Sabiha N Qazi
(74) *Attorney, Agent, or Firm* — Andrus Intellectual Property Law, LLP

(57) ABSTRACT

Disclosed are 19-nor-vitamin D compounds, and specifically seco-A-2,19-dinor-1,25-dihydroxyvitamin $D_3$ as well as pharmaceutical uses therefor. These compounds exhibit relatively high activity in vivo, specifically in intestinal tissues, but relatively low VDR binding activity, cell differentiation activity and gene transcription activity. There is thus potential for these compounds to have strong cell selectivity for use as therapeutic agents against some cancers, such as colon cancer or polyps, as well as hyperplastic intestinal disorders, such as Crohn's disease, ulcerative colitis and celiac disease. These compounds also have relatively high intestinal calcium transport activity evidencing potential in the treatment of bone diseases.

35 Claims, 5 Drawing Sheets

HL-60 Cell Differentiation $EC_{50}$: $1,25(OH)_2D_3 = 3 \times 10^{-9}$ M
DA2HE = $3 \times 10^{-7}$ M

(56) References Cited

OTHER PUBLICATIONS

Yusheng, et al., "A Practical Synthesis of 14-epi-19-nor-1alpha,25-Dihydroxyvitamin D3 Analogues and Their A-ring Epimers", Journal of Organic Chemistry, 2001, 3779-37886.

International Search Report and Written Opinion, PCT International Application No. PCT/US2013/042659, mailed Sep. 11, 2013.

Arbour et al., "A Highly Sensitive Method for Large-Scale Measurements of 1,25-Dihydroxyvitamin D", Analytical Biochemistry, 1998, 255: 148-154.

Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.

Collins et al., "Normal Functional Characteristics of Cultured Human Promyelocytioc Leukemia Cells (HL-60) After Induction of Differentiation by Dimethylsulfoxide", The Journal of Experimental Medicine, 1979, 149: 969-974.

Glebocka et al., "New 2-Alkylidene 1Alpha,25-Dihydroxy-19-norvitamin D3 Analogues of High Intestinal Activity: Synthesis and Biological Evaluation of 2-(3'-Alkoxypropylidene) and 2-(3'-Hydroxyproplidene) Derivatives", J. Med. Chem, 2006, 49: 2909-2920.

Grzywacz et al., "2-Methylene Analogs of 1alpha-hydroxy-19-norvitamin D3; Synthesis, Biological Activities of Docking to the Ligand Binding Domain of the Rat Vitamin D Receptor", J. Steroid Biochem, 2004, 89-90: 13-17.

Inhoffen et al., "Studies in the Vitamin D Series,XXI: Hydrine Compounds from Bitamin D3", Chemische Berichte, 1957, 90: 664-673.

Kittaka et al., "Efficient and Convergent Coupling Route for the Short-step Synthesis of Enantiopure 2alpha- and 2beta-Alkylated 1alpha,25-Dihydroxy-19-Norvitamin D3 Analogues", Synlett, 2003, 8: 1175-1179.

Kittaka et al., "Efficient Synthesis of of 2-Modified 1alpha,25-Dihydroxy-19-Norvitamin D3 with Julia Olefination: High Potency in Induction of Differentiation on HL-60 Cells", J. Org. Chem, 2003, 68: 7407-7415.

Miyamoto et al., "Synthetic Studies of Vitamin D Analogs. XIV. Synthesis and Calcium Regulating Activity of Vitamin D3 Analogs Bearing a Hydroxyalkoxy Group at the 2beta-Position", Chem. Pharm. Bull., 1993, 41(6): 1111-1113.

Nishii et al., "The Development of Vitamin D3 Analogs for the Treatment of Osteoporosis", Osteoporosis International, 1993, 1: 190-193.

Okano et al., "Regulatory Activites of 2beta-(3-Hydroxypropoxy)-1alpha,25-Dihydroxyvitamin D3, A Novel Synthetic Vitamin D3 Derivative, on Calcium Metabolism", Biochem. Biophys. Res. Commun., 1989, 163(3): 1444-1449.

Osterm et al., "24- and 26-homo-1,25-dihydroxyvitamin D3: Preferential Activity in Inducing Differentiation of Human Leukemia Cells HL-60 in vitro", Proc. Natl. Acad. Sci. USA, 1987, 84: 2610-2614.

Perlman et al., "1alpha,25-dihyroxyvitamin D3, a Novel Vitamin D-related Compound with Potential Therapeutic Activity", Tetrahedron Letters, 1990, 31: 1823-1824.

Perlman et al., "Novel Synthesis of 19-Nor-Vitamin D Compounds", Tetrahedron Letters, 1991, 32: 7663-7666.

Posner et al., "Stereocontrolled Total Synthesis of Calcitrol Derivatives: 1,25-Dihyroxy-2-(4'-hydroxybutyl)vitamin D3 Analogs of an Osteoporosis Drug", Journal of Organic Chemistry, 1994, 59: 7855-7861.

Posner et al., "2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing", Journal of Organic Chemistry, 1995, 60: 4617-4626.

Sicinski et al., "New Highly Calcemic 1alpha,25-dihydroxy-19-Norvitamin D3 Compounds with Modified Side Chain: 26,27-dihomo- and 26,27-dimethylene Analogs in 20S-Series", Steroids, 2002, 67: 247-256.

Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.

Windaus et al., "The Constitution of Vitamin D2: Part II", Annalen der Chemie, 1936, 524: 295-299.

Armesto et al., "Efficient synthesis of (−)-methyl 3-epi-shikimate and methyl 3-epi-quinate by one-pot selective protection of trans-1,2-diols", Tetrahedron Letters, 2000, 41: 8759-8762.

Soriente et al., "Enzymatic Desymmetrization of a Prochiral 1,3,5-Pentanetriol Derivative. Application to the Synthesis of a Cyanobacterial Heterocyst Glycolipid", Tetrahedron: Asymmetry, 1995, 6(4): 859-862.

* cited by examiner

A-RING MODIFIED 19-NOR-VITAMIN D ANALOGS AND THEIR USES

CROSS-REFERENCE TO RELATED APPLICATIONS

The present application claims the benefit of priority to U.S. Provisional Patent Application No. 61/656,157, filed on Jun. 6, 2012, the content of which is incorporated herein by reference in its entirety.

BACKGROUND

The field of the invention relates to vitamin D compounds, and more particularly to 19-nor-Vitamin D analogs and their pharmaceutical uses, and especially seco-A-2,19-dinor-1,25-dihydroxyvitamin $D_3$, its biological activities, and its pharmaceutical uses. This latter compound can also be abbreviated simply as "DA2HE."

The natural hormone, $1\alpha,25$-dihydroxyvitamin $D_3$ and its analog in the ergosterol series (i.e., $1\alpha,25$-dihydroxyvitamin $D_2$) are known to be highly potent regulators of calcium homeostasis in animals and humans, and their activity in cellular differentiation has also been established. (See Ostrem et al., Proc. Natl. Acad. Sci. USA, 84, 2610 (1987)). Many structural, analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. These differences in activity may be useful in the treatment of a variety of diseases such as renal osteodystrophy, vitamin D-resistant rickets, osteoporosis, psoriasis, and certain malignancies.

Another class of vitamin D analogs, i.e., the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment, of malignancies, or the treatment of various skin disorders. Two different methods of synthesis of such 19-nor-vitamin D analogs have been described. (See Perlman et al., Tetrahedron Lett. 31, 1823 (1990); Perlman et al., Tetrahedron Lett. 32, 7663 (1991); and DeLuca et al., U.S. Pat. No. 5,086,191).

In U.S. Pat. No. 4,666,634, 2β-hydroxy and alkoxy (e.g., ED-71) analogs of $1\alpha,25$-dihydroxyvitamin $D_3$ have been described and examined by the Chugai group as potential drugs for osteoporosis and as antitumor agents. (See also Okano et al., Biochem. Biophys. Res. Commun. 163, 1444 (1989)). Other 2-substituted (e.g., with hydroxyalkyl, (ED-120) and fluoroalkyl groups) A-ring analogs of $1\alpha,25$-dihydroxyvitamin $D_3$ have also been prepared and tested. (See Miyamoto et al., Chem. Pharm. Bull. 41, 1111 (1993); Nishii et al., Osteoporosis Int. Suppl. 1, 190 (1993); and Posner et al., J. Org. Chem. 59, 7855 (1994), and J. Org. Chem. 60, 4617(1995)).

2-substituted analogs of $1\alpha,25$-dihydroxy-19-nor-vitamin $D_3$ have also been synthesized, for example compounds substituted at the 2-position with hydroxy or alkoxy groups, (see DeLuca et al., U.S. Pat. No. 5,536,713), with 2-alkyl groups, (see DeLuca et al. U.S. Pat. No. 5,945,410), and with 2-alkylidene groups, (see DeLuca et al. U.S. Pat. No. 5,843,928). These 2-substituted analogs exhibit interesting and selective activity profiles. All these studies indicate that binding sites on vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached at carbon 20 (C-20) have also been synthesized and tested. $1\alpha$-hydroxy-2-methylene-19-nor-pregnacalciferol is described in U.S. Pat. No. 6,566,352. $1\alpha$-hydroxy-2-methylene-19-nor-homopregnacalciferol is described in U.S. Pat. No. 6,579,861, and $1\alpha$-hydroxy-2-methylene-19-nor-bishomopregnacalciferol is described in U.S. Pat. No. 6,627,622. All three of these compounds have relatively high binding activity to vitamin D receptors and relatively high cell differentiation activity. However, these compounds have little if any calcemic activity as compared to $1\alpha,25$-dihydroxyvitamin $D_3$. Their biological activities make these compounds excellent candidates for a variety of pharmaceutical uses, as set forth in the '352, '861 and '622 patents.

Analogs of the natural hormone $1\alpha,25$-dihydroxyvitamin $D_3$ characterized by the transposition of the A-ring exocyclic methylene group from carbon 10 (C-10) to carbon 2 (C-2) (e.g., $1\alpha,25$-dihydroxy-2-methylene-19-nor-vitamin D analogs) have been synthesized and tested. (See Sicinski et al., J. Med. Chem., 41, 4662 (1998); Sicinski et al., Steroids 67, 247 (2002); and DeLuca et al., U.S. Pat. Nos. 5,843,928; 5,936,133 and 6,382,071)). In these studies, it was found that $1\alpha,25$-dihydroxy-2-methylene-19-nor-vitamin D analogs are characterized by significant biological potency. In addition, the biological potency of such analogs may be enhanced dramatically where "unnatural" (20S)-configuration is present.

SUMMARY

Disclosed herein are vitamin D compounds characterized by lacking the A-ring exocyclic methylene group at carbon 10 (C-10), (i.e., a class of 19-nor vitamin D compounds), and also characterized by the presence of a seco-A ring. These analogs also lack a carbon 2 (C-2) group, and thus the present invention is directed toward 19-nor-vitamin D analogs, and their pharmaceutical uses, and more specifically toward seco-A-2,19-dinor-1,25-dihydroxyvitamin $D_3$, its biological activity, and various pharmaceutical uses for this compound.

Structurally these 19-nor-vitamin D analogs are characterized by the general formula I shown below:

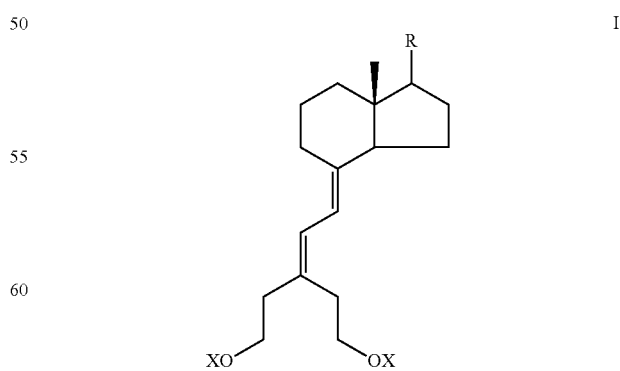

where X is selected from the group consisting of hydrogen and a hydroxy-protecting group. R represents any of the typical side chains known for vitamin D type compounds or hydrogen, alkyl, hydroxyalkyl, or fluoroalkyl group. For example, R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis (Z) or trans (E) geometry, and where Y is selected from hydrogen, methyl, —COR$^5$ and a radical of the structure:

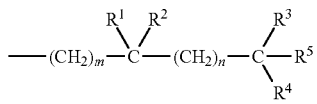

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, may bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, may bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

Specific important examples of side chains are the structures represented by formulas (a), (b), (c), (d) and (e) below with natural 20R-configuration, i.e., the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

Additional important examples of side chains are the structures represented by formulas (a), (b), (c), (d) and (e) below having the 20-epi or 20S-configuration, i.e., the side chain as it occurs in (20S)-25-hydroxyvitamin D$_3$ (a); (20S)-vitamin D$_3$ (b); (20S)-25-hydroxyvitamin D$_2$ (c); (20S)-vitamin D$_2$ (d); and the C-24 epimer of (20S)-25-hydroxyvitamin D$_2$ (e).

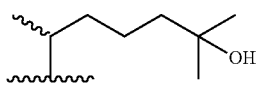

(a)

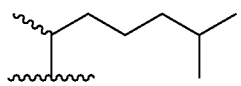

(b)

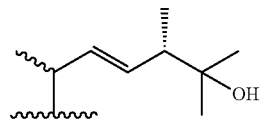

(c)

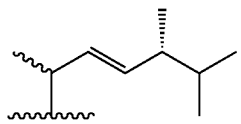

(d)

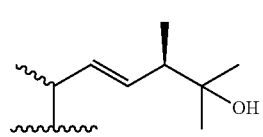

(e)

The wavy line to the carbon 20 indicates that carbon 20 may have either the R or S configuration.

A preferred analog as disclosed herein is seco-A-2,19-dinor-1,25-dihydroxyvitamin D$_3$ (which is referred to herein as "DA2HE") which has the following formula Ia;

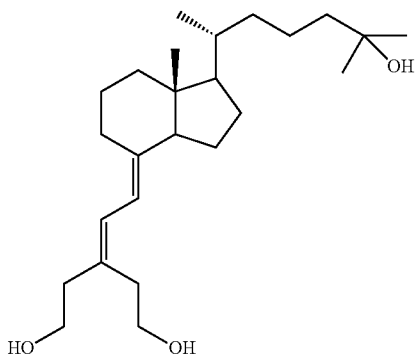 [SMILES: C[C@H](CCCC(C)(C)O)C1CCC2/C(=C/C=C(CCO)CCO)CCC[C@@]21C]

Ia

The above compounds of formula I, especially formula Ia, exhibit a desired, and highly advantageous, pattern of biological activity. These compounds are characterized by relatively low binding to vitamin D receptors as compared to 1,25(OH)$_2$D$_3$. These compounds also exhibit markedly lower in vitro transcription activity as well as significantly less potency for causing differentiation of HL-60 cells than 1,25(OH)$_2$D$_3$. These compounds also exhibit relatively low activity in their ability to mobilize calcium from bone, but relatively high ability to promote intestinal calcium transport, as compared to 1α,25-dihydroxyvitamin D$_3$.

These compounds exhibit significant biological activity profiles in vivo, specifically in intestinal tissue. This is likely due to these compounds maintaining two hydroxyl groups in the approximate same location as the natural hormone 1α;25-dihydroxyvitamin D$_3$. Accordingly, these analogs may serve as important therapies for metabolic bone diseases where intestinal calcium transport activity is desirable, such as bone diseases like senile osteoporosis, postmenopausal osteoporosis, steroid-induced osteoporosis, low bone turnover osteoporosis, osteomalacia, and renal osteodystrophy.

Because DA2HE showed surprisingly high biological activity in vivo, specifically in intestinal tissue, but relatively low activities in promyelocytic leukemia cells and osteosarcoma cells, there is potential for this compound and the compounds of formula I to have a strong selectivity for some cell types. Such cell selectivity could make DA2HE and the compounds of formula I an important therapeutic choice for treatment or prevention of some types of cancers, such as colon cancer, or polyps, as well as hyperplastic intestinal disorders, such as Crohn's disease, ulcerative colitis and celiac disease.

One or more of the compounds may foe present in a pharmaceutical composition to treat and/or prevent the above-noted diseases in an amount from about 0.01 μg/gm to about 1000 μg/gm of the composition, preferably from about 0.1 μg/gm to about 500 μg/gm of the composition. The pharmaceutical compositions typically may be administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of DA2HE and 1,25$(OH)_2D_3$ to compete for binding with [$^3$H]-1,25-$(OH)_2D_3$ to the full-length recombinant rat vitamin D receptor.

FIG. 2 is a graph illustrating the percent HL-60 cell differentiation as a function of the concentration of DA2HE and 1,25$(OH)_2D_3$.

FIG. 3 is a graph illustrating the in vitro transcription activity of DA2HE and 1,25$(OH)_2D_3$.

FIG. 4 is a bar graph illustrating the bone calcium mobilization activity of DA2HE and 1,25$(OH)_2D_3$.

DETAILED DESCRIPTION OF THE INVENTION

Figure 1:
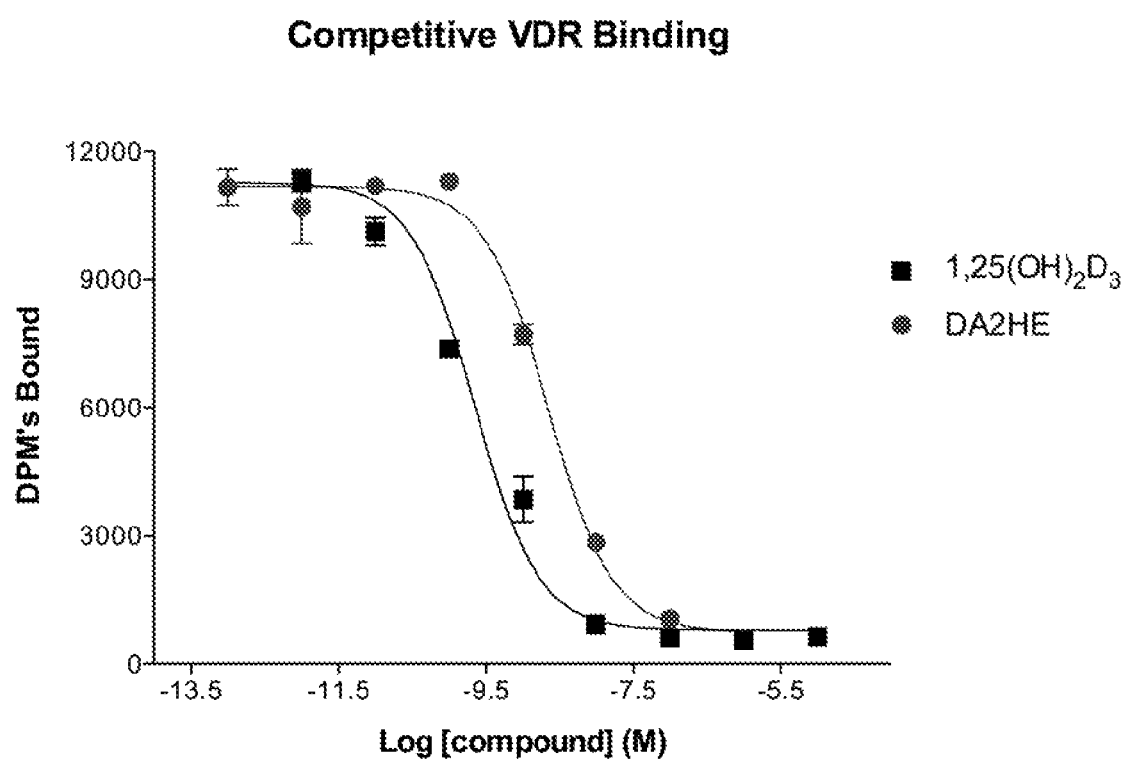
FIGS. 1-4 illustrate various biological activities of seco-A-2,19-dinor-1,25dihydroxy vitamin $D_3$, herein referred to as "DA2HE," as compared to the native hormone 1α,25-dihydroxyvitamin $D_3$, herein "1,25$(OH)_2D_3$."

Disclosed are vitamin D analogs, and more particularly 19-nor-Vitamin D analogs and their pharmaceutical uses, and especially seco-A-2,19-dinor-1,25-dihydroxyvitamin $D_3$, its biological activities, and its pharmaceutical uses.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. If a definition in this specification is contrary to a definition in a referenced publication or patent, the definition in this specification should be utilized to construe the meaning of the claims and the disclosure. All references cited in this specification are to be taken as indicative of the level of skill in the art. Nothing herein is to be construed as an admission that the invention is not entitled to antedate such disclosure by virtue or prior invention.

In the specification and in the claims, the terms "including" and "comprising" are open-ended terms and should be interpreted to mean "including, but not limited to." These terms encompass the more restrictive terms "consisting essentially of" and "consisting of." It is also to be noted that the terms "comprising," "including," "characterized by" and "having" can be used interchangeably.

As used herein, and in the appended claims, the singular forms "a" "an," and "the" include plural reference unless the context clearly dictates otherwise. As well, the terms "a" (or "an"), "one or more" and "at least one" can be used interchangeably herein.

Where a range of values is provided, it is understood that each intervening value, and any combination or subcombination of intervening values, between the upper and lower limit of that range and any other stated or intervening value in that stated range, is encompassed within the range of values recited.

Certain terms or ranges may be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number, and thus will typically refer to a number or value that is 10% below or above the specifically recited number or value.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatized or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 19-nor-vitamin D analogs of the basic structure I can be accomplished by a common general method, i.e., the Julia olefination involving a coupling of an unsaturated sulfone IV (easily prepared from a bicyclic Windaus-Grundmann type ketone III) with the ketone V:

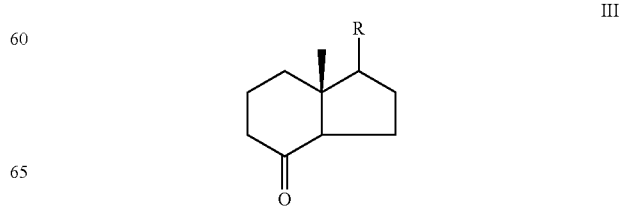

-continued

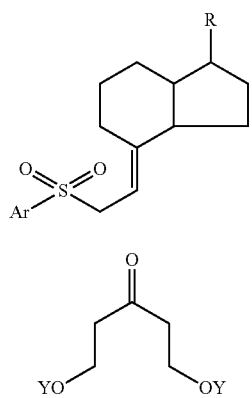

IV

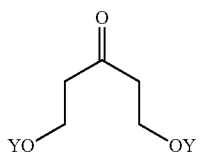

V

In the structures III, IV and V groups Y and R represent groups defined above whereas Ar represents phenyl, substituted phenyl, benzothiazol-2-yl (preferably) and other aromatic groups that can be suitable for the Julia olefination process, it being also understood that any functionalities in Ar that might be sensitive, or that interfere with the condensation reaction, should be avoided. The process shown above represents an application of the convergent synthesis concept, which has been applied effectively for the preparation of vitamin D compounds. (See, e.g., Kittaka et al., Synlett 8, 1175 (2003), and J. Org. Chem., 68, 7407 (2003).

Bicyclic hydrindanone compounds of the general structure III are known, or can be easily prepared by known methods from the corresponding Windaus-Grundmann type ketones. Specific important examples of such known bicyclic ketones are the structures with the side chains (h), (i), (j), (k), (l), (m), and (n) below described above, i.e., 25-hydroxy Grundmann's ketone (h) (see Baggiolini et al., J. Org. Chem., 51, 3098 (1986)); Grundmann's ketone (i) (see Inhoffen et al., Chem. Ber., 90, 664 (1957)); 25-hydroxy Windaus ketone (j) (see Baggiolini et al., J. Org. Chem., 51, 3098 (1986)); Windaus ketone (k) (see Windaus et al., Ann., 524, 297 (1936)); (20S)-25-hydroxy Grundmann's ketone (I) (see Sicinski et al., J. Med. Chem., 41, 4662 (1998)); (20S)-Grundmann's ketone (m) (see Grzywacz et al., J. Steroid Biochem. Mol. Biol., 89-90, 13 (2004)); and (20S)-25-methyl Grundmann's ketone (n) (see Grzywacz et al., J. Steroid Biochem. Mol. Biol., 89-90, 13 (2004)):

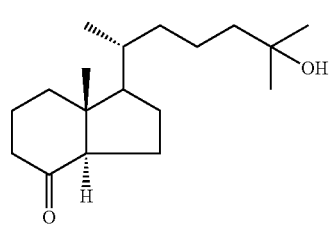

(h)

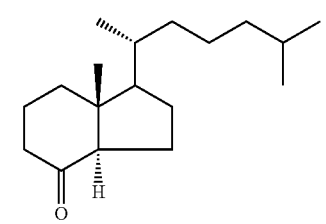

(i)

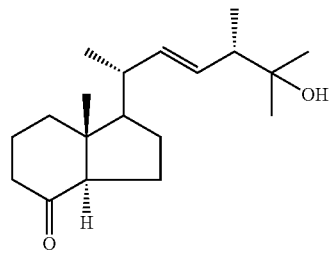

(j)

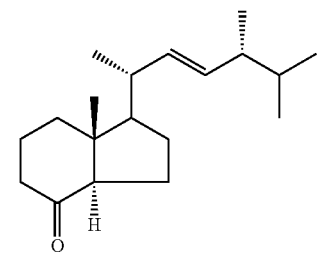

(k)

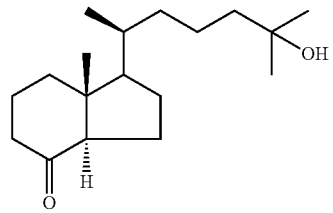

(l)

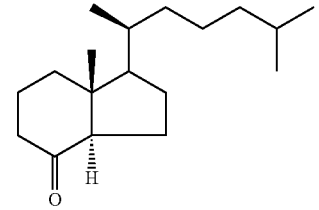

(m)

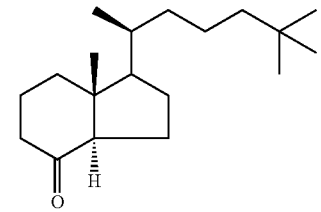

(n)

The preparation of the required ketone of structure V was accomplished starting from the acetic acid 5-acetoxy-3-(t-butyl-dimethyl-silanyloxy)-pentyl ester (1), that was prepared from penta-1,4-dien-3-ol, according to a known procedure. (See A. Scoriente et al., Tetrahedrom Asymmetry, 6, 4, 859 (1995)). Transformation of 1 into the desired ketone of the general structure V is shown in SCHEME I. Thus, the secondary t-butyldimethylsilyl group in 1 was hydrolyzed under TBAF condition leading to the hydroxyl compound 2, which was next oxidized with pyridinium chlorochromate to the desired ketone 3. The latter compound was then subjected to modified Julia Olefination with the anion generated with lithium bis(trimethylsilyl)amide from benzothiazolyl sulfone 4, prepared form the corresponding Grundmann ketone according to the known procedure. (See Glebocka et al., J. Med. Chem., 49, 2909 (2006)). Removal of the protecting groups in the obtained bis-seco-steroid gave the expected vitamin D derivative 5 which was purified by HPLC.

Several other vitamin D compounds characterized by the A-seco structure may be synthesized by the method disclosed herein using the ketone 3 and the appropriate CD-fragments derived from the Windaus-Grundmann ketones having the desired side chain structure.

This invention is described by the following illustrative examples. In these examples specific products identified by Arabic numerals (e.g. 1, 2, 3, etc.) refer to the specific structures so identified in the preceding description and in the SCHEME I.

EXAMPLES

The following examples are illustrative and should not be construed to limit the scope of the claims.

Chemistry. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 400 and 500 MHz with a Broker DMX-400 and Bruker DMX-500 spectrometers, respectively. $^{13}$C nuclear magnetic resonance (NMR) spectra were recorded at 100 and 125 MHz with the same spectrometers in deuteriochloroform. Chemical shifts ($\delta$) were reported downfield from internal Me$_4$Si ($\delta$0.00). Electron impact (EI) mass spectra were obtained with a Micromass AutoSpec (Beverly, Mass.) instrument. High-performance liquid chromatography (HPLC) was performed on a Waters Associated liquid chromatography equipped with a Model 6000A solvent delivery system, a Model U6K Universal injector, and a Model 486 tunable absorbance detector. THF was freshly distilled before use from sodium benzophenone ketyl under argon.

Example 1

Preparation of Vitamin D Analog 5

Hydrolysis of t-butyldimethylsilyl Group 1 (SCHEME 1) and Preparation of Acetic Acid 5-acetoxy-3-hydroxy-pentyl ester (2).

The starting bicyclic compound 1 was obtained according to the described procedure. (See Armesto et al., Tetrahedron Letters 41, 8759 (2000)). Compound 1 (70 mg, 0.220 mmol) was dissolved in anhydrous THF (5 mL) and treated with TBAF (1M in THF; 350 µmol). The solution was stirred at room temperature under argon for 2 h, poured into brine, and extracted with ethyl acetate. The extract was washed with brine, dried (Na$_2$SO$_4$) and evaporated. The obtained product was purified by silica gel chromatography. Elution with hexane/ethyl acetate (1:1) gave pure, colorless oily hydroxy compound 2 (32 mg, 71%).

2: $^1$H NMR (400 MHz, CDCl$_3$) $\delta$ 1.73 and 1.82 (2×3H, each m, 2-H$_2$ and 4-H$_2$), 2.07 (6H, S, COCH$_3$), 3.77 (1H, m, 3-H), 4.16 and 4.33 (2×2H, each m, 1-H$_2$ and 5-H$_2$); $^{13}$C NMR $\delta$ 21.0 (COCH$_3$), 36.3 (C2 and C4), 61.5 (C1 and C5), 65.4 (C3), 171.5 (COCH$_3$); ESI MS for C$_9$H$_{16}$O$_5$Na (M+Na)$^+$ 227.2.

Oxidation of Hydroxyl Group in 2 and Preparation of Acetic Acid 5-acetoxy-3-oxo-pentyl ester (3).

A suspension of 2 (31 mg, 0.152 mmol) and pyridinium chlorochromate (65 mg, 0.30 mmol) in anhydrous CH$_2$Cl$_2$ (2 mL) was stirred at room temperature for 5 h, then filtered through a pad a silica gel. The pad was washed with ethyl acetate to give ketone 3 (28 mg, 90%).

3: $^1$H NMR (400 MHz CDCl$_3$) $\delta$ 2.79 (4H, t, J=6.2, 2-H$_2$ and 4-H$_2$), 2.04 (6H, s, COCH$_3$), 4.35 (4H, T, J=6.2, 1-H$_2$ and 5-H$_2$); $^{13}$C NMR $\delta$ 20.8 (COCH$_3$), 42.7 (C2 and C4), 59 (C1 and C5), 171.5 (COCH$_3$); 204.7 (C3), ESI MS for C$_9$H$_{14}$O$_5$Na (M+Na)$^+$ 225.2.

Julia Coupling of Ketone 3 with Sulfone 4 to Prepare 3,5-Seco-2,19-bisnor Analog of 1$\alpha$,25-dihydroxyvitamin D$_3$ (5).

To a solution of sulfone 4 (54.0 mg, 89 µmol) in dry THF (700 µL), LiHMDS (1 M in THF; 90 µL, 90 µmol) was added at −78° C. under argon. The solution turned deep red. The mixture was stirred at −78° C. for 5 min, and a solution of ketone 3 (9 mg, 44.5 µmol) in THF (200+100 µL) was added. The reaction mixture was stirred at −78° C. for 2.5 h, then brine containing 1% HCl was added, and the mixture was poured into brine and extracted with ethyl acetate. The extract was washed with brine, dried (Na$_2$SO$_4$), and evaporated. The yellow oily residue was applied on a silica column, eluted with hexane/ethyl acetate (9:1) and concentrated under vacuum. The oily product was dissolved in anhydrous dry MeOH (1.2 ml) and treated with (+)-camphorsulfonic acid (20 mg, 86 µmol). The solution was stirred at room temperature under argon for 24 h, poured into brine, and extracted with ethyl acetate. The extract was washed with, brine, dried (Na$_2$SO$_4$) and evaporated. The obtained product was purified by straight-phase HPLC (9.4 mm×25 cm Zorbax Rx-Sil column, 4 mL/min) using hexane/IPA (8:2) solvent system; 3,5-Seco-2,19-dinor analog of 1$\alpha$,25-(OH)$_2$D$_3$ 5 (4.5 mg, 26%) was collected at R$_v$ 23 mL. Additional purification was accomplished by reversed-phase HPLC (9.4 mm×25 cm Zorbax XDB, C-18 column, 4 mL/min) using MeOH/H$_2$O (9:1) solvent system; the analog 5 (4.5 mg, 26%) was collected at R$_v$ 23 mL.

5: UV (in EtOH) $\lambda_{max}$ 250.5 nm; $^1$H NMR (400 MHz, CDCl$_3$) $\delta$ 0.544 (3H, s, 18-H$_3$), 0.940 (3H, d, J=6.3 Hz, 21-H$_3$), 1.219 (6H, s, 26- and 27-H$_3$), 2.38 and 2.49 (2×2H, each t, J=6.3 Hz, 4- and 10-H$_3$), 2.81 (1H, br d, J=12.2 Hz, 9$\beta$-H), 3.75 (4H, t, J=6.3 Hz, 1- and 3-H$_2$), 5.85 and 6.38 (1H and 1H, each d, J=11.1 Hz, 7- and 6-H); HRMS (ESI) exact mass calculated for C$_{25}$H$_{44}$O$_3$Na (M+Na)+415.6174, measured 415.6179.

SCHEME 1.

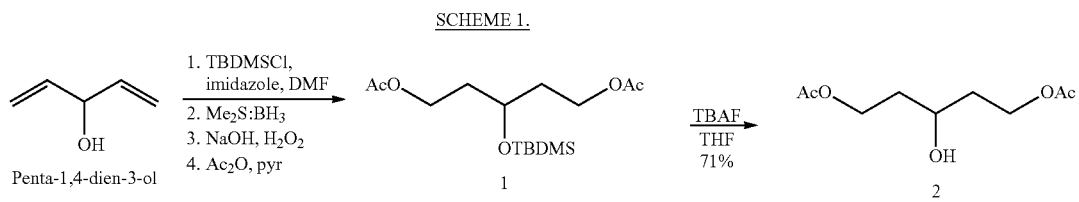

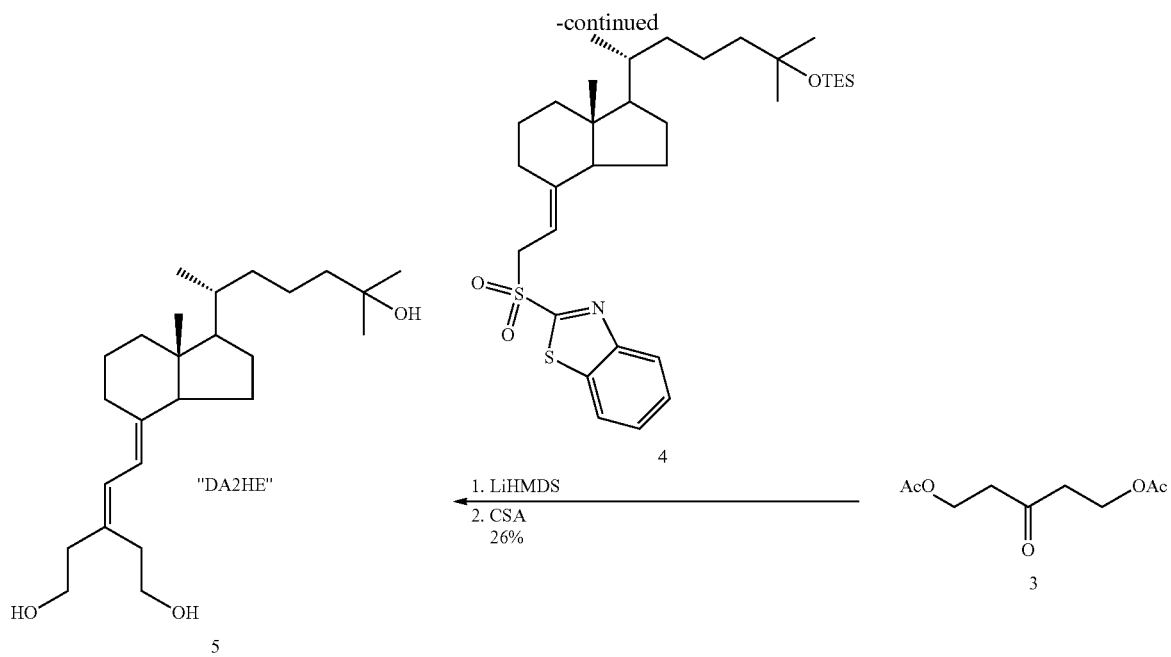

Example 2

Biological Activity of Seco-A-2,19-dinor-1,25-dihydroxyvitamin $D_3$ (DA2HE)

Figure 2:
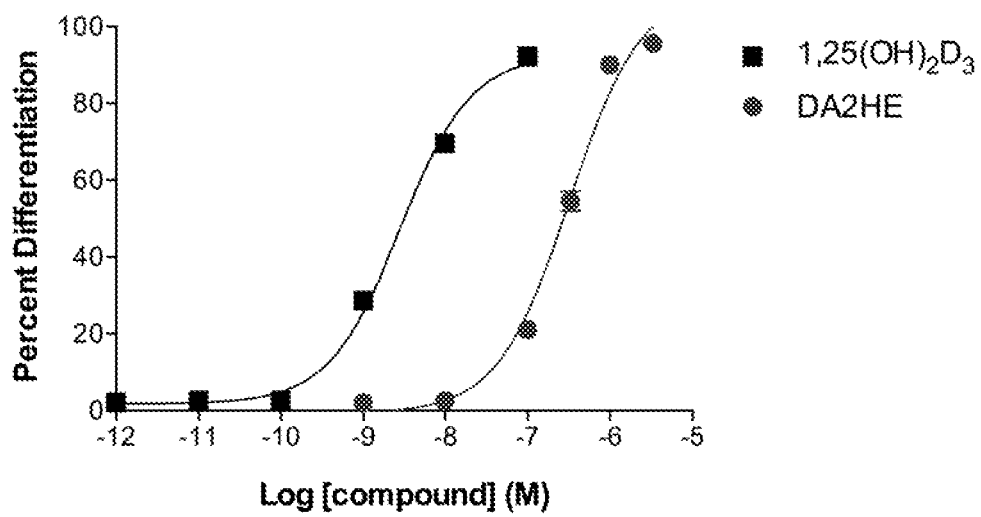
Figure 3:
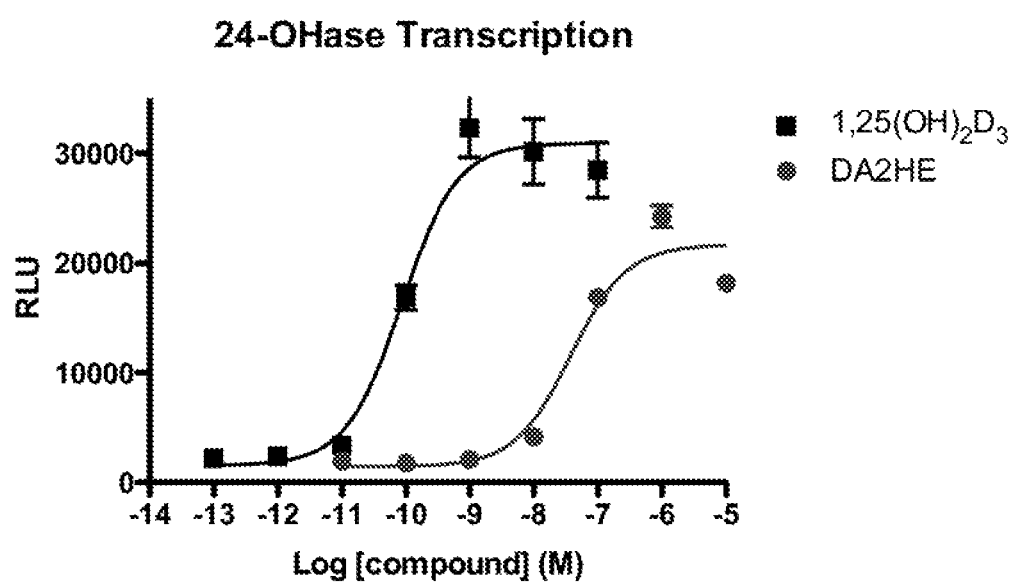

Elimination of the A-ring of 1α,25-dihydroxyvitamin $D_3$ by removing carbon 2 (C-2) while maintaining two hydroxyl groups in the approximate same location as the natural vitamin D hormone had significant effect on binding to the full length recombinant rat vitamin D receptor (VDR), as compared to 1α,25-dihydroxyvitamin $D_3$. The compound DA2HE bound to the VDR with about one log less activity as compared to the standard 1α,25-$(OH)_2D_3$ (FIG. 1). This result might suggest that compound DA2HE would have little or insignificant biological activity. As shown in FIG. 2, DA2HE is 100 times less potent than 1,25$(OH)_2D_3$ on HL-60 cell differentiation, and as shown in FIG. 3, DA2HE is 500 times less potent than the native hormone in stimulation of gene transcription.

Figure 4:
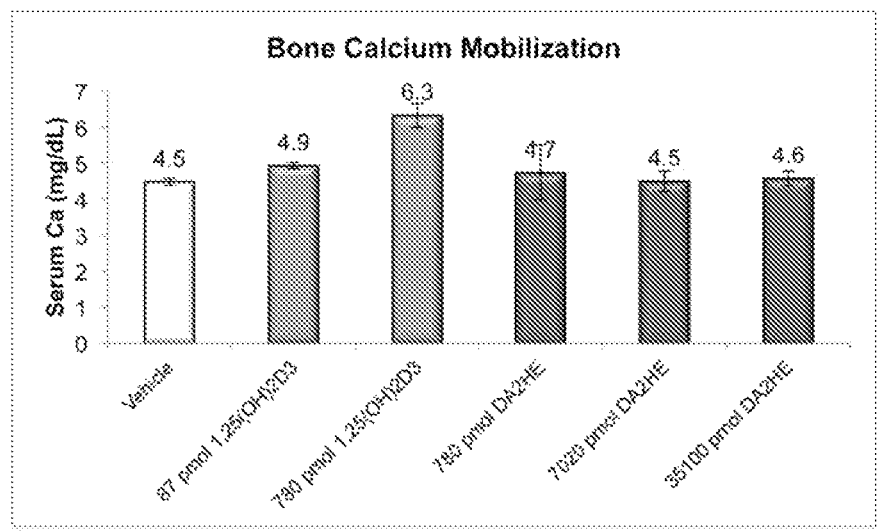
Figure 5:
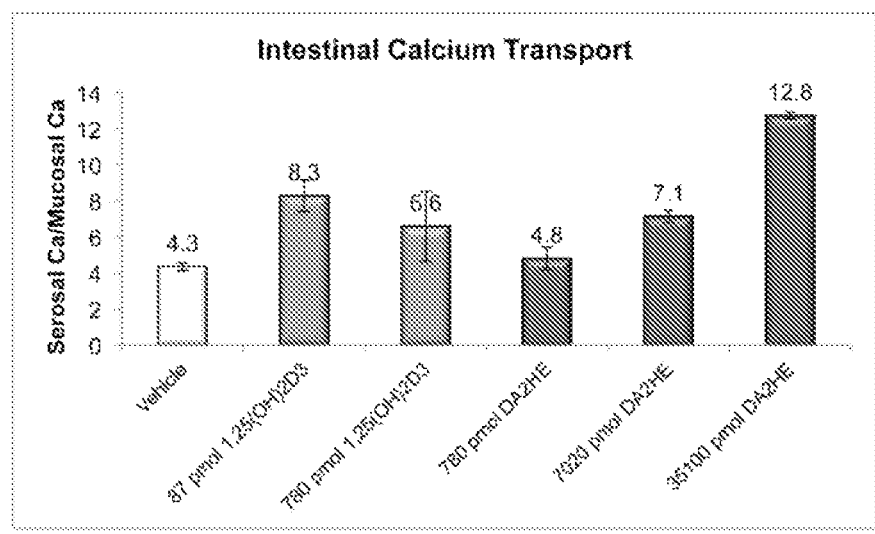
FIG. 5 is a bar graph Illustrating the intestinal calcium transport activity of 1,25$(OH)_2D_3$ as compared to DA2HE.

However, DA2HE was observed to have a unique biological activity with respect to calcemic activity. As shown in FIG. 4, DA2HE lacks any bone calcium mobilization activity, as compared to 1,25$(OH)_2D_3$, even after up to 35100 pmol was administered intraperitoneally one time daily for four consecutive days. Surprisingly, however, FIG. 5 shows that DA2HE has relatively high activity as compared to that of 1α,25-dihydroxyvitamin $D_3$ (1α,25$(OH)_2D_3$), the natural hormone, in stimulating intestinal calcium transport, DA2HE is only about 10 times less potent than 1α,25$(OH)_2D_3$ in promoting active calcium transport across the gut. FIGS. 4-5 thus illustrate that DA2HE may be characterized as having relatively high intestinal calcium activity, but no bone calcium mobilization activity.

Experimental Methods

The compounds of the invention were prepared and studied using the following methods.

Vitamin D Receptor Binding
Protein Source.
Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs.
Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$, ~159 Ci/mmole) was added in ethanol at a final concentration of 1 nM.

Assay Conditions. Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, phi 7.4) containing 0.5% Triton X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Study Drugs.
The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells.

Human promyelocyte leukemia (HL60) cells were grown in RPMI-1640 medium containing 10% fetal bovine serum. The cells were incubated at 37° C. in the presence of 5% $CO_2$.

Assay Conditions.

HL60 cells were plated at $1.2 \times 10^5$ cells/ml. Eighteen hours after plating, cells in duplicate were treated with drug. Four days later, the cells were harvested and a nitro blue tetrazolium reduction assay was performed. (See Collins et al., 1979: J. Exp. Med. 149:969-974), The percentage of differentiated cells was determined by counting a total of 200 cells and recording the number that, contained intracellular black-blue formazan deposits. Verification of differentiation to monocytic cells was determined by measuring phagocytic activity.

In Vitro Transcription Assay.

Transcription activity was measured in ROS 1.7/2.8 (bone) cells that were stably transfected with a 24-hydroxylase (24 Ohase) gene promoter upstream of a luciferase reporter gene. (See Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (see Suda et al., J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR Binding, HL60 Cell Differentiation, and Transcription Activity.

DA2HE ($K_i=4\times10^{-10}$M) has about 10 times less activity as the natural hormone 1α,25-dihydroxyvitamin $D_3$ ($K_i=4\times10^{-11}$M) in its ability to compete with [$^3$H]-1,25(OH)$_2O_3$ for binding to the full-length recombinant rat vitamin D receptor (FIG. 1). DA2HE is also about 100 times less potent ($EC_{50}=3\times10^{-7}$M) in its ability (efficacy or potency) to promote HL60 differentiation as compared to 1α,25-dihydroxyvitamin $D_3$ ($EC_{50}=3\times10^{-9}$M) (See FIG. 2). Also, DA2HE is about 500 times less potent ($EC_{50}=4\times10^{-8}$M) than 1α,25-dihydroxyvitamin $D_3$ ($EC_{50}=8\times10^{-11}$M) in stimulation of gene transcription in bone cells (FIG. 3).

Calcium Mobilization from Bone and Intestinal Calcium Absorption in Vitamin D-Deficient Animals.

Using vitamin D-deficient rats on a low calcium diet (0.02%), the activities of DA2HE and 1,25(OH)$_2O_3$ in intestine and bone were tested. As expected, the native hormone (1,25(OH)$_2D_3$) increased serum calcium levels at the dosages tested (FIG. 4). FIG. 4 also shows that DA2HE lacks any activity in mobilizing calcium from bone at the tested doses. Administration of DA2HE at 35100 pmol/day for 4 consecutive days resulted in no mobilization of bone calcium.

Intestinal calcium transport was evaluated in the same groups of animals using the everted gut sac method (FIG. 5). These results show that the compound DA2HE only has slightly less ability to promote intestinal calcium transport activity when administered at the recommended lower dosages, as compared to 1,25(OH)$_2O_3$. Thus, it may be concluded that DA2HE has relatively high intestinal calcium transport activity which increases in a dose dependent manner.

In vivo distinct activity profiles emerge most likely due to these compounds maintaining two hydroxyl groups in the approximate same location as the natural hormone 1α,25-dihydroxyvitamin $D_3$. These analogs may serve as important therapies for metabolic bone diseases where intestinal calcium transport activity is desirable, such as bone diseases like senile osteoporosis, postmenopausal osteoporosis, steroid-induced osteoporosis, low bone turnover osteoporosis, osteomalacia, and renal osteodystrophy.

Because DA2HE showed surprisingly high activity in vivo, specifically in intestinal tissue, but relatively low activities in promyelocytic leukemia cells and osteosarcoma cells, there is potential for this compound and the compounds of formula I to have a strong selectivity for some cell types. Such cell selectivity could make, DA2HE and the compounds for formula I an important therapeutic choice for treatment or prevention of some types of cancers such as colon cancer, or polyps, as well as hyperplastic intestinal disorders, such as Crohn's disease, ulcerative colitis and celiac disease.

For prevention and/or treatment purposes, the compounds of this invention, defined by formula I, and Ia may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilisers, anti-oxidants, binders, coloring agents or emulsifying or taste-modifying agents.

The compounds of formula I and particularly DA2HE of formula Ia, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, particularly DA2HE, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds L particularly DA2HE, as defined by the above formula I, and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg/day, and preferably from about 0.1 μg/day to about 500 μg/day.

The compounds I, particularly DA2HE, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly DA2HE, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

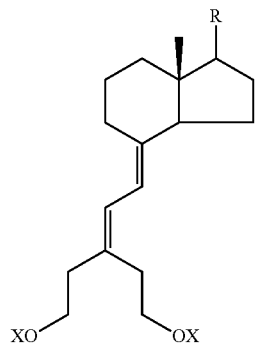

where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

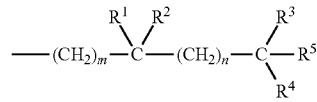

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

2. The compound of claim 1 wherein X is hydrogen.

3. The compound of claim 1 wherein R is selected from:

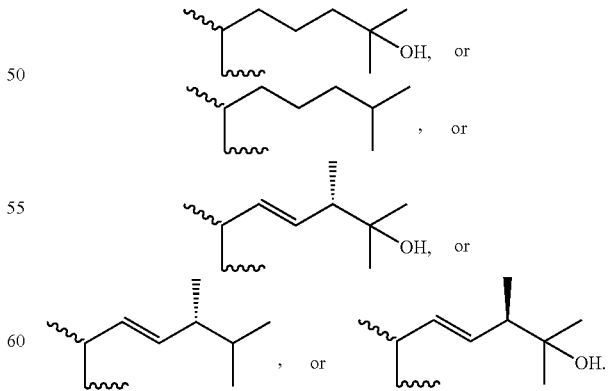

4. The compound of claim 3 wherein X is hydrogen.

5. A pharmaceutical composition containing an effective amount of at least one compound as claimed in claim 1 together with a pharmaceutically acceptable excipient.

6. The pharmaceutical composition of claim 5 wherein said effective amount composes from about 0.01 μg to about 1000 μg per gram of composition.

7. The pharmaceutical composition of claim 5 wherein said effective amount comprises from about 0.1 μg to about 500 μg per gram of composition.

8. A compound having the formula:

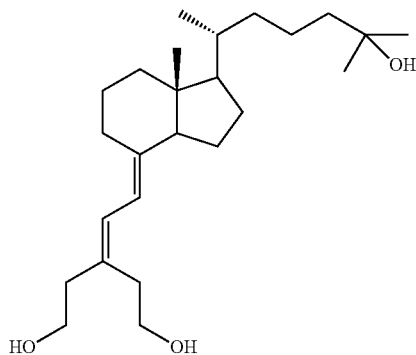

and named seco-A-2,19-dinor-1,25-dihydroxyvitamin $D_3$.

9. A pharmaceutical composition containing an effective amount of seco-A-2,19-dinor-1,25-dihydroxyvitamin $D_3$ together with a pharmaceutically acceptable excipient.

10. The pharmaceutical composition of claim 9 wherein said effective amount comprises from about 0.01 μg to about 1000 μg per gram of composition.

11. The pharmaceutical composition of claim 9 wherein said effective amount comprises from about 0.1 μg to about 500 μg per gram of composition.

12. A method of treating a disease selected from the group consisting of colon cancer, Crohn's disease, ulcerative colitis, and celiac disease comprising administering to a subject with said disease an effective amount of a 19-nor-vitamin D having the formula:

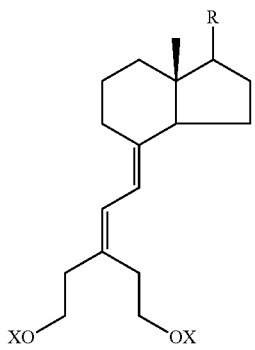

where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

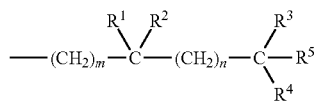

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group =$CR^2R^3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

13. The method of claim 12 wherein the vitamin D is administered orally.

14. The method of claim 12 wherein the vitamin D is administered parenterally.

15. The method of claim 12 wherein the vitamin D is administered transdermally.

16. The method of claim 12 wherein the vitamin D is administered rectally.

17. The method of claim 12 wherein the vitamin D is administered nasally.

18. The method of claim 12 wherein the vitamin D is administered sublingually.

19. The method of claim 12 wherein the vitamin D is administered in a dosage of from about 0.01 μg/day to about 1000 μg/day.

20. The method of claim 12 wherein the vitamin D has the formula:

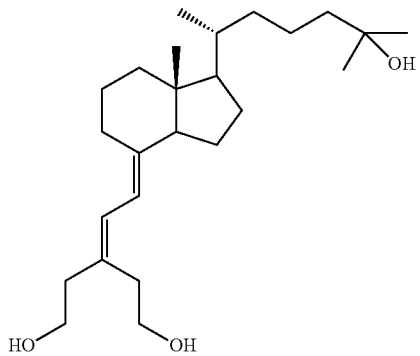 [SMILES: C[C@H](CCCC(C)(C)O)C1CCC2/C(=C/C=C(CCO)CCO)CCC[C@@]21C]

and is named seco-A-2,19-dinor-1,25-dihydroxyvitamin $D_3$.

21. A method of treating metabolic bone disease where it is desired to maintain or increase bone mass comprising administering to a patient with said disease an effective amount of a compound having the formula:

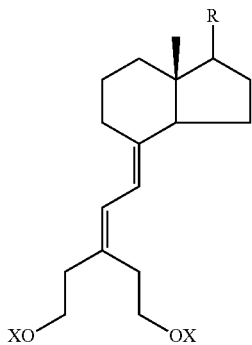

where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure;

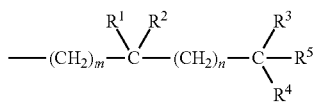

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

22. The method of claim 21 wherein the compound is administered orally.

23. The method of claim 21 wherein the compound is administered parenterally.

24. The method of claim 21 wherein the compound is administered transdermally.

25. The method of claim 21 wherein the compound is administered rectally.

26. The method of claim 21 wherein the compound is administered nasally.

27. The method of claim 21 wherein the compound is administered sublingually.

28. The method of claim 21 wherein the compound is administered in a dosage of from about 0.01 μg/day to about 1000 μg/day.

29. The method of claim 21 where the disease is senile osteoporosis.

30. The method of claim 21 where the disease is postmenopausal osteoporosis.

31. The method of claim 21 where the disease is steroid-induced osteoporosis.

32. The method of claim 21 where the disease is low bone turnover osteoporosis.

33. The method of claim 21 where the disease is osteomalacia.

34. The method of claim 21 where the disease is renal osteodystrophy.

35. The method of claim 21 wherein the compound has the formula:

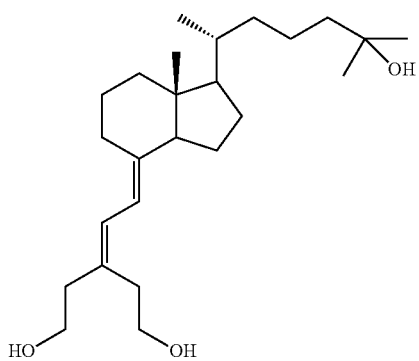 [SMILES: C[C@H](CCCC(C)(C)O)C1CCC2/C(=C/C=C(CCO)CCO)CCC[C@@]21C]

and is named seco-A-2,19-dinor-1,25-dihydroxyvitamin D$_3$.

* * * * *